(12) United States Patent
Kim (10) Patent No.: US 10,568,719 B2
(45) Date of Patent: Feb. 25, 2020

(54) DENTAL PROSTHESES

(71) Applicant: DENTCA, Inc., Torrance, CA (US)

(72) Inventor: Tae Hyung Kim, La Canada, CA (US)

(73) Assignee: DENTCA, Inc., Torrance, CA (US)

( * ) Notice: Subject to any disclaimer, the term of this patent is extended or adjusted under 35 U.S.C. 154(b) by 0 days.

(21) Appl. No.: 15/806,248

(22) Filed: Nov. 7, 2017

(65) Prior Publication Data
US 2018/0125614 A1    May 10, 2018

Related U.S. Application Data

(60) Provisional application No. 62/419,419, filed on Nov. 8, 2016.

(51) Int. Cl.
*A61C 8/00* (2006.01)
*A61C 13/225* (2006.01)

(52) U.S. Cl.
CPC .......... *A61C 8/0048* (2013.01); *A61C 8/0068* (2013.01); *A61C 8/0095* (2013.01); *A61C 13/225* (2013.01)

(58) Field of Classification Search
CPC .... A61C 8/0048; A61C 8/0068; A61C 13/225
See application file for complete search history.

(56) References Cited

U.S. PATENT DOCUMENTS

| | | | | |
|---|---|---|---|---|
| 4,767,328 A | * | 8/1988 | Branemark | A61C 8/0048 433/168.1 |
| 5,064,374 A | * | 11/1991 | Lundgren | A61C 8/0048 433/173 |
| 5,219,286 A | * | 6/1993 | Hader | A61C 8/0048 433/172 |
| 5,419,700 A | * | 5/1995 | Sillard | A61C 8/0048 433/172 |
| 5,575,651 A | * | 11/1996 | Weissman | A61C 8/0048 433/173 |
| 5,885,078 A | | 3/1999 | Cagna et al. | |

(Continued)

FOREIGN PATENT DOCUMENTS

DE    20201981    7/2002
EP     2106768    10/2009

OTHER PUBLICATIONS

PCT International Application No. PCT/KR2017/060682, International Search Report dated Feb. 19, 2018, 11 pages.

(Continued)

*Primary Examiner* — Ralph A Lewis
(74) *Attorney, Agent, or Firm* — Lee, Hong, Degerman, Kang & Waimey (57) ABSTRACT

Disclosed is an apparatus for implant-bar-supported restoration that includes a superstructure and a plurality of dental bars. At least two of the plurality of dental bars have different shapes or different sizes, and the superstructure is coupled with the plurality of dental bars. Also disclosed is a dental bar including a plurality of separate pieces, wherein: each of the plurality of pieces is shaped and configured to be coupled with a dental implant; each of the plurality of pieces is shaped and configured to be coupled with a superstructure; and each of the plurality of pieces has a different shape or different size.

20 Claims, 5 Drawing Sheets

(56) References Cited

U.S. PATENT DOCUMENTS

| | | | |
|---|---|---|---|
| 6,056,547 A * | 5/2000 | Names | A61C 8/0001 |
| | | | 433/173 |
| 6,506,052 B1 * | 1/2003 | Hoffman | A61C 8/0048 |
| | | | 433/181 |
| 6,692,254 B1 * | 2/2004 | Kligerman | A61C 8/0048 |
| | | | 433/173 |
| 7,021,934 B2 * | 4/2006 | Aravena | A61C 1/084 |
| | | | 433/173 |
| 8,277,216 B2 | 10/2012 | Kim | |
| 8,899,983 B2 | 12/2014 | Kim | |
| 8,998,615 B2 | 4/2015 | Kim | |
| 2004/0038181 A1 | 2/2004 | Fortin | |
| 2010/0183998 A1 | 7/2010 | Poirier et al. | |
| 2015/0164620 A1 | 6/2015 | Berger | |
| 2015/0230891 A1 | 8/2015 | Grobbee et al. | |

OTHER PUBLICATIONS

European Patent Office Application Serial No. 17870434.2, Search Report dated Oct. 22, 2019, 9 pages.

\* cited by examiner

DENTAL PROSTHESES

CROSS-REFERENCE TO RELATED APPLICATIONS

Pursuant to 35 U.S.C. 119(e), this application claims the benefit of U.S. Provisional Patent Application No. 62/419,419, filed on Nov. 8, 2016, the contents of which are hereby incorporated by reference herein in its entirety.

FIELD OF THE INVENTION

The present invention relates to an implant-supported dental restoration, and more particularly, to an implant-bar-supported dental restoration for partially or fully edentulous patients.

DESCRIPTION OF RELATED ART

A conventional implant-bar-supported dental restoration, such as implant bar overdenture and screw-retained fixed denture, is one of treatments available for partially or fully edentulous patients. Typically, the conventional implant-bar-supported restoration requires a single bar coupled to a plurality of implants. The bar firmly supports and stabilizes a superstructure, which increases chewing efficiency and bite force compared with standard removable dentures. However, the conventional bar having a single-body structure is difficult to manipulate because the single-body structured bar must connect with a plurality of implants at various positions of the bar, requiring highly trained skill, and often causing complexity in bar shapes, thus making clinical procedures complicated and technically difficult. For instance, even a minor gap generated between the bar and the implant requires reproduction of the entire bar. To prevent such a problem, dentists need to precisely measure and record the implant locations.

A bar of "fixed denture" is wrapped by ceramics or acrylic material to be fixed with a superstructure. This structure could provide higher stability compared with other prosthesis structures. However, repair and maintenance of such a conventional bar become more costly and complicated. For example, in case that the superstructure of fixed denture has a crack or teeth get damaged, the superstructure and the bar need to be taken off from a patient's mouth to be repaired at a dental laboratory.

Furthermore, a patient has to make a plurality of visits to a dentist to receive the conventional implant-bar-supported dental restoration. Such visits are necessary in order for a dentist to take an impression of the patient's gums and a bite registration, and to review a try-in superstructure and bars.

For example, during first and second visits, a dentist examines a patient and takes a preliminary alginate impression and a final impression. At a dental laboratory, a master gum model is created and a base plate is fabricated based on the final impression received from the dentist. Then, a bite registration rim or block, usually made of wax, is fabricated from the master gum mold. The master gum mold, with the bite registration rim attached thereto, is sent back to the dentist.

During a third visit, the bite registration rim is inserted into the mouth of the patient, and adjusted inside the mouth to determine maxilla-mandibular relations and to take a bite registration. Further, artificial teeth to be used for the superstructure are selected by the dentist and the patient. The adjusted bite registration rim is sent back to the dental laboratory to fabricate a wax try-in for superstructure. The laboratory returns the wax try-in with the actual final teeth lined up along the outer edge of the wax rim.

During a fourth visit, the dentist examines how the wax try-in looks and works in the patient, checking occlusal and vertical dimensions. If adjustments are necessary, the wax try-in can be sent back to the laboratory to reset the teeth. In dental laboratory, the wax try-in is adjusted and a dental bar is fabricated according to the implant locations and its type. The fabricated dental bar is sent to the dentist.

During a fifth visit, the dentist examines whether the dental bar can fit implants and implant abutments properly. If adjustments are necessary, the bar is sent back to the laboratory with the adjustment instruction to adjust or change the shape to fit the implants.

Until the fabricated bar fits the patient's mouth properly, the bar try-in and adjustment process is repeated. After confirming the proper fitting of the bar, dental laboratory modifies the wax try-in to fit the bar and invests the wax try-in and converts to acrylics to fabricate the final superstructure. Finally, the superstructure and the bar are delivered to the dentist to be put on the patient.

While such implant-bar-supported dentures and the process of using the same have been proven to be useful, there is a desire to continue to improve the design and fabrication process of an implant-bar-supported denture.

BRIEF SUMMARY OF THE INVENTION

According to one exemplary embodiment of the present invention, an apparatus for implant-bar-supported restoration includes a superstructure and a plurality of dental bars. In one aspect of the present invention, at least two of the plurality of dental bars have different shapes or different sizes. In further aspect of the present invention, the superstructure is coupled with the plurality of dental bars.

According to another exemplary embodiment of the present invention, a dental bar includes a plurality of separate pieces, wherein: each of the plurality of pieces is shaped and configured to be coupled with a dental implant; each of the plurality of pieces is shaped and configured to be coupled with a superstructure; and each of the plurality of pieces has a different shape or different size.

BRIEF DESCRIPTION OF THE DRAWINGS

The drawings, which are incorporated herein, illustrate one or more embodiments of the present invention, thus helping to better explain one or more aspects of the one or more embodiments. As such, the drawings are not to be construed as limiting any particular aspect of any embodiment of the invention.

DETAILED DESCRIPTION

In general, the present invention relates to an implant-bar-supported restoration. The implant-bar-supported restoration is for full- or partial-arch restoration.

Figure 1A:
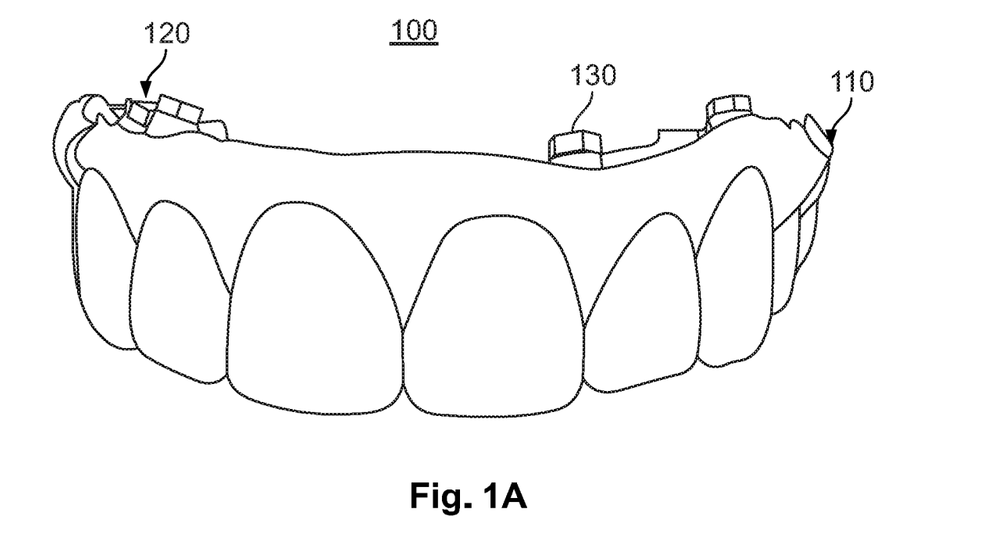
FIG. 1A shows a facial view of an example of an implant-bar-supported restoration according to an embodiment of the present invention.
Figure 1B:
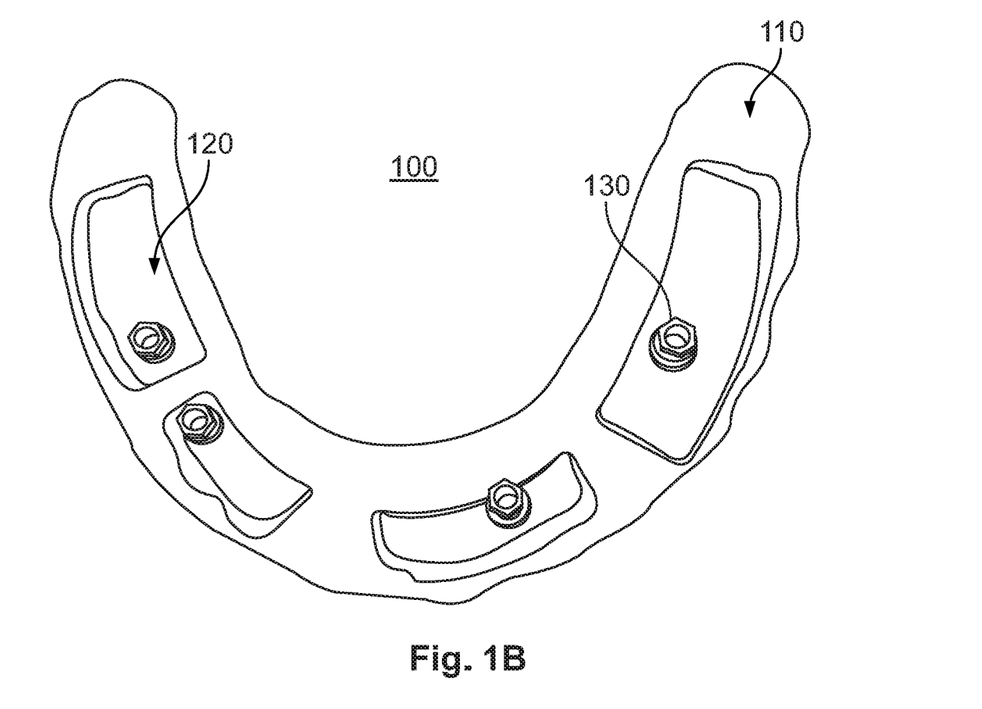
FIG. 1B shows a bottom view of an implant-bar-supported restoration according to an embodiment of the present invention.

In one embodiment of the present invention, as illustrated in FIG. 1A and FIG. 1B, the apparatus for implant-bar-supported dental restoration 100 includes a superstructure 110 and a plurality of dental bars 120. For example, in FIG. 1A and FIG. 1B, four dental bars 120 are coupled to the superstructure 110. Each of the plurality of dental bars 120 is separated from another dental bar.

Although the number of dental bars 120 is shown as four in FIG. 1A and FIG. 1B, the number is not limited to four and may vary depending on patients. That is, the number of dental bars 120 depends on a size and a shape of the superstructure. In one example embodiment of the present invention, the plurality of dental bars 120 includes at least two dental bars and more preferably includes at least three or four dental bars to support a full-arch superstructure. Further, each or at least one of the plurality of dental bars 120 is curved according to the curved shape of the superstructure.

Figure 2A:
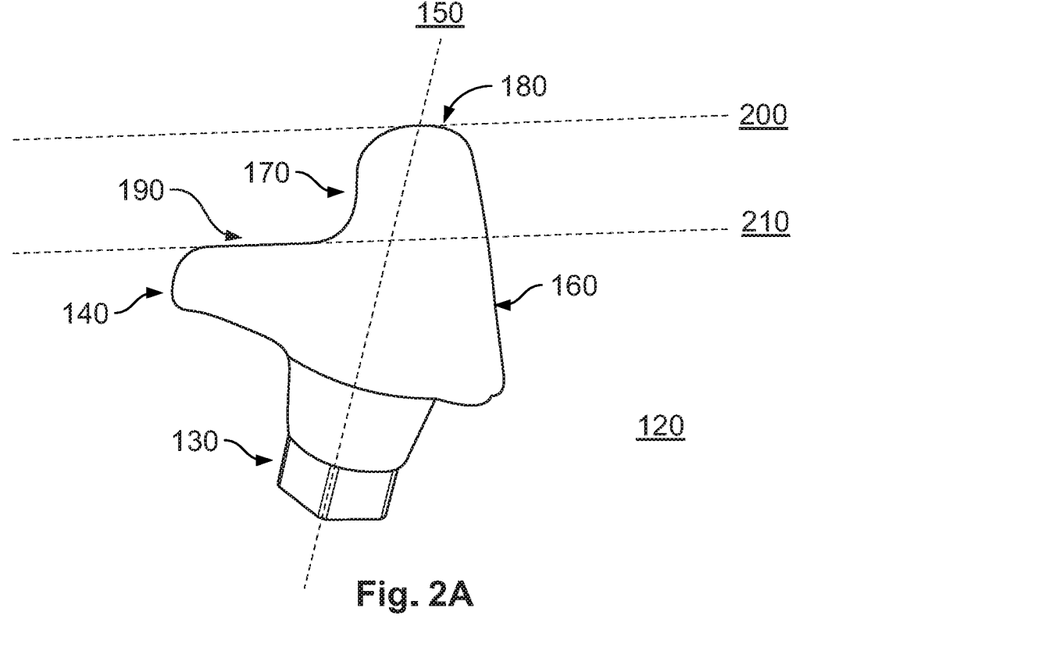
FIGS. 2A and 2B are distal side views of a dental bar according to an embodiment of the present invention.
Figure 2B:
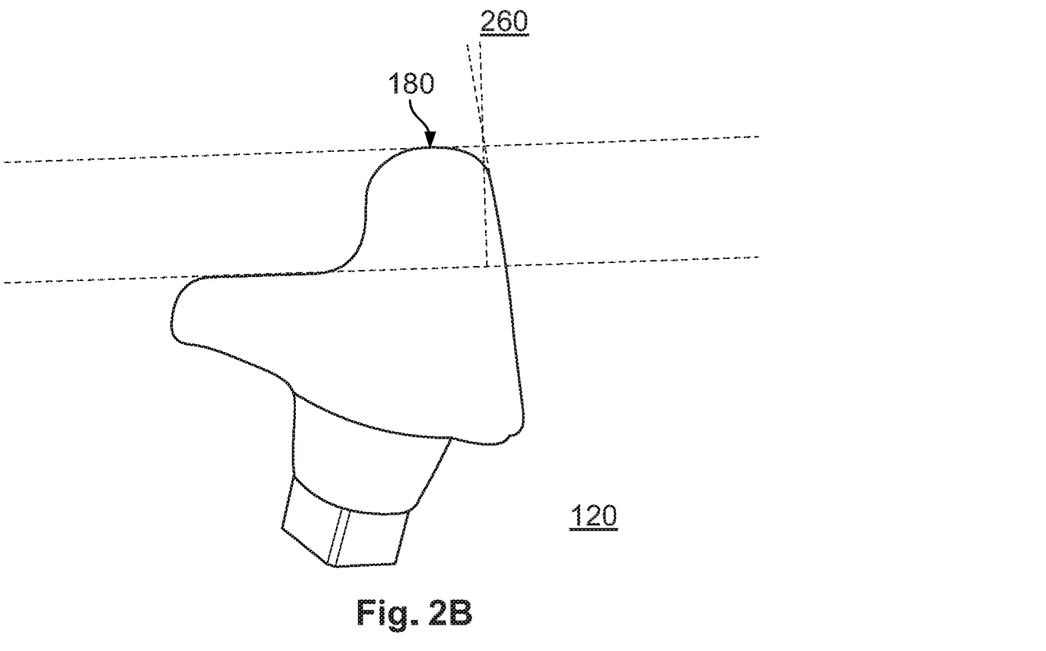
Figure 2C:
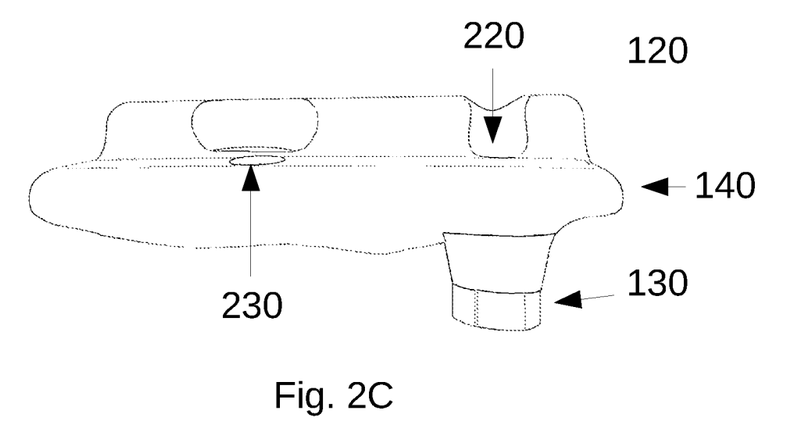
FIG. 2C is a lingual view of a dental bar according to an embodiment of the present invention.

In one embodiment of the present invention, as illustrated in FIG. 2A, FIG. 2B, and FIG. 2C, a single dental bar 120 includes at least one implant interface 130 and a beam structure 140. The implant interface 130 is shaped and configured to be inserted into a dental implant. In one aspect of the present invention, the implant interface 130 is protrudingly formed from a bottom surface of the beam structure 140. Also see FIG. 1B.

For example, a dental implant fixed to a patient's gum has a receiving portion that is shaped and configured to receive the implant interface 130 of the dental bar 120. The dental bar 120 is securely coupled to the dental implant by a screw that passes through a through hole formed at the beam structure 140 and the implant interface 130 of the dental bar 120, the screw tightened into the receiving portion of the dental implant. In one embodiment, the central axis 150 of the implant interface 130 is aligned with the central axis of the dental implant when the implant interface 130 is properly inserted into the receiving portion of the dental implant.

Buccal side surfaces 160 of all beam structures 140 have a substantially same inclination with respect to top surfaces 180 of the beam structure 140 or occlusal plane for proper placement of the superstructure 110 onto the dental bars 120. Typically, the angulation of the beam structure 140 is not in parallel with respect to the central axis 150 of the implant interface 130, but is inclined with respect to the central axis 150 of the implant interface 130. See FIG. 2A.

Lingual side surfaces 170 of all beam structures 140 also have approximately same angulations with respect to the top surfaces 180 or occlusal plane. The buccal side surface 160 and the lingual side surface 170 may form a tapered shape as illustrated in FIG. 2A and FIG. 2B. For example, the degree of the inclination of the buccal side surface 160 is less than about 30 degree with respect to the imaginary line 260 which is perpendicular to the top surface 180. The beam structure 140 may further include at least one step structure on buccal, lingual, mesial or distal side. FIG. 2A illustrates a step structure on lingual side including the top surface 180 and a lower surface 190 to support the superstructure 110. The imaginary line 200 of the top surface 180 and the imaginary line 210 of the lower surface 190 may be in parallel.

Figure 2D:
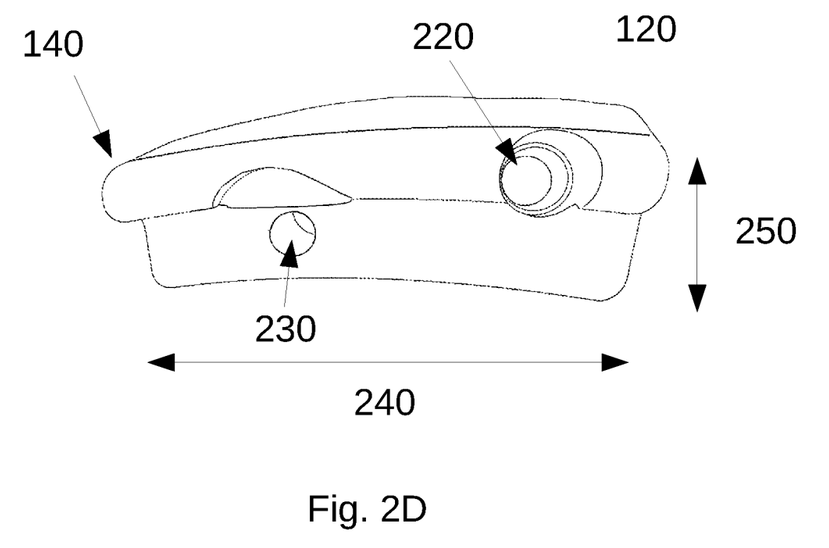
FIG. 2D is a top view of a dental bar according to an embodiment of the present invention.

The dental bar 120 further includes at least one structure that is configured or shaped to be coupled to at least one dental implant. Examples of the structures configured to be coupled to the dental implant by the open hole are external joint type, internal joint type or taper joint type. Referring to FIG. 2A, in one example embodiment of the present invention, the implant interface 130 is shaped to be coupled with or inserted into a top portion of the dental implant. In further example embodiment of the present invention, the dental bar 120 further includes at least one through hole, through which one or more screws pass, such that the one or more screws are screwed into the at least one dental implant. As illustrated in FIG. 2C and FIG. 2D, the through hole 220 is formed through the beam structure 140 and the implant interface 130. The through hole 220 is configured to receive a fastening means such as a screw which is screwed into the dental implant to securely fix the dental bar 120 onto the dental implant.

With reference to FIG. 2D, an example of a dimension of the dental bar 120 is illustrated. The length 240 of dental bar 120 may be less than 40 mm and the width 250 of the dental bar 120 may be at least 3 mm. However, the length 240 and width 250 of the dental bar 120 are not limited thereto.

Figure 3A:
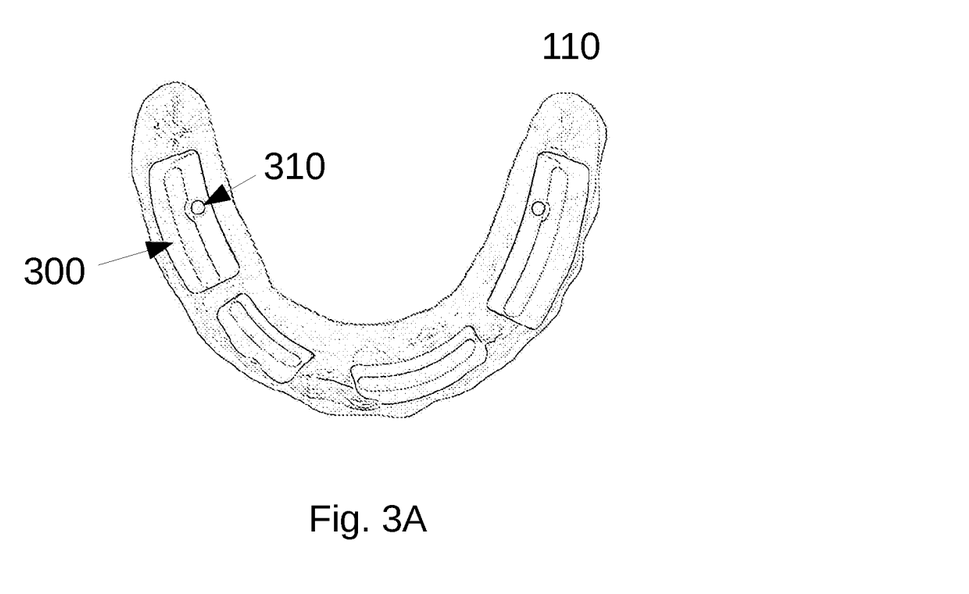
FIG. 3A is a bottom view of a superstructure used in an implant-bar-supported restoration according to an embodiment of the present invention.

Referring to FIG. 3A, the superstructure 110 includes at least one housing space 300 on mucosal surface to receive the dental bars 120. In one example embodiment of the present invention, as illustrated in FIG. 3A, the superstructure 110 includes a plurality of housing spaces 300 to receive dental bars 120. Each housing space 300 may be shaped to fit the corresponding dental bar 120. The housing space 300 may have at least 50 μm margin on each of the buccal, lingual, mesial, distal and top side. Preferably, the margin may be at least 100 μm on each of the buccal, lingual, mesial, distal and top side, and more preferably, the margin may be at least 200 μm on each of the buccal, lingual, mesial and distal side and 100 μm on the top side.

Figure 3B:
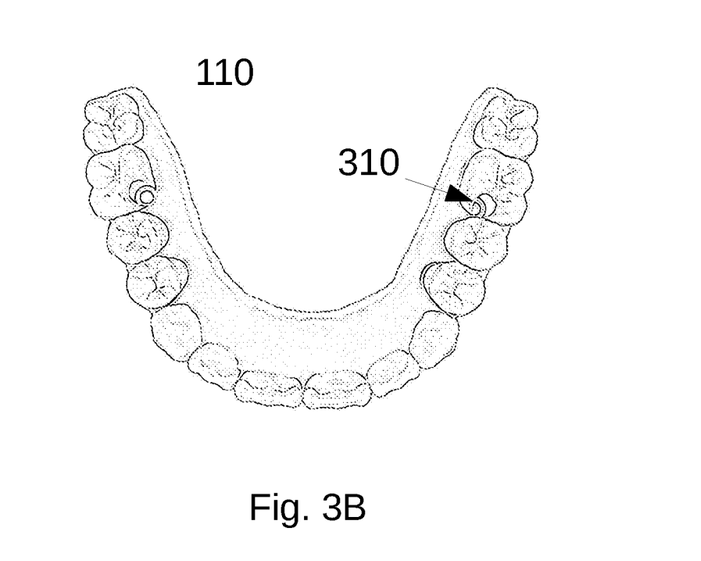
FIG. 3B is a top view of the superstructure shown in FIG. 3A.

The superstructure 110 is engaged with the dental bars 120 by a mechanical, physical and/or chemical method. In one example embodiment of the present invention, the superstructure 110 and at least one dental bar 120 are engaged by a screw. As illustrated in FIG. 3A and FIG. 3B, the housing space 300 includes at least one screw hole 310. Referring to FIG. 2C and 2D, the dental bar 120 includes at least one screw hole 230. Screw hole 310 and/or 230 may include a thread groove to be engaged with the screw. One or more screws are placed and tightened through the screw holes 310 and 230 to securely couple the superstructure 110 with the at least one dental bar 120.

Figure 4:
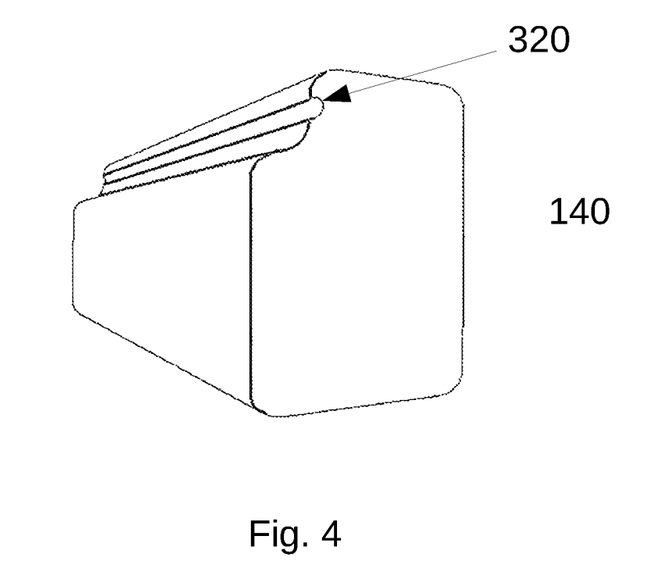
FIG. 4 is a lingual perspective view of a portion of a dental bar according to another embodiment of the present invention.

In another example embodiment of the present invention, at least one of dental materials, such as denture base resin, dental cement, dental adhesive or dental resin for temporary restoration, is applied to the housing space 300. Once the dental material is cured after the superstructure 110 is placed onto dental bars 120, the superstructure 110 is securely engaged with the dental bars 120. In further example embodiment, the beam structure 140 of the dental bar 120 may include at least one groove or recession 320 which is configured to be filled with the dental material for further engagement. As illustrated in FIG. 4, the beam structure 140 may include at least one groove 320 on buccal, lingual, mesial and/or distal surface. The depth of the groove or recession 320 is preferably less than 2 mm.

Figure 5:
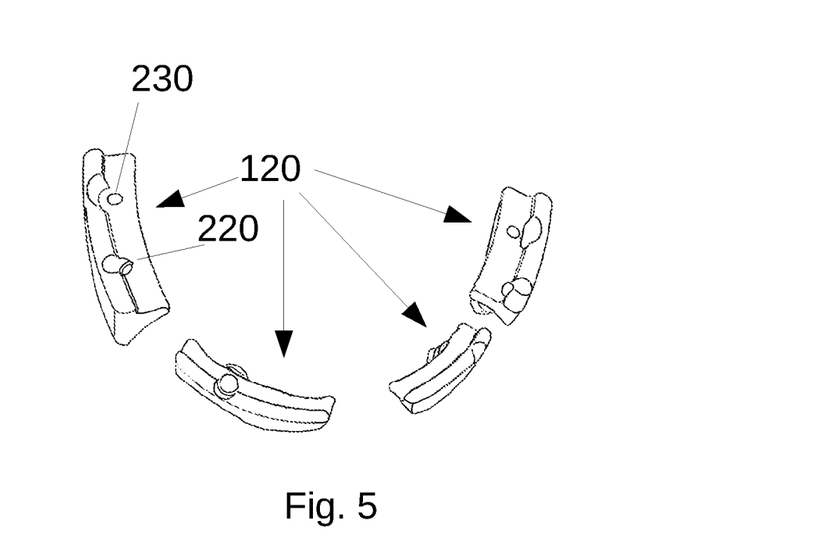
FIG. 5 is a top perspective view of dental bars of an implant-bar-supported restoration according to an embodiment of the present invention.

In one example embodiment, as illustrated in FIG. 5, at least two of dental bars 120 of the implant-bar-supported restoration have different shapes and/or different sizes. Preferably, each of the plurality of dental bars has a different shape or different size.

In one example embodiment, the superstructure 110 is made of acrylic polymer. In another embodiment, the superstructure 110 is made of ceramics or zirconia. In one example embodiment, the dental bar 120 is made of metal such as titanium or cobalt-chrome.

In one embodiment of the present invention, a method for fabrication of the implant-bar-supported restoration is provided. The method includes 1) obtaining digital records of first impressions of upper and lower jaws of a patient's mouth and implant's position and orientation, 2) obtaining a digital record of a relationship between the upper and lower jaws, 3) digitally designing a try-in superstructure and a plurality of dental bars of the upper or lower jaw, 4) fabricating the try-in superstructure and dental bars, 5) taking a second impression of the upper or lower jaw connecting with the dental bars by the try-in superstructure, 6) obtaining a digital record of the second impression, 7) digitally adjusting the superstructure design, and 8) fabricating a final superstructure of the upper or lower jaw.

During step 1, dental impressions of upper and lower jaws with impression copings may be physically taken. The physical impressions with impression copings are scanned to make the digital record. The physical impressions may be directly scanned or a stone model of the impression may be scanned. Alternatively, the upper and/or patient jaw where scan bodies are placed onto implants is intra-orally scanned.

During step 2, in one example embodiment, upper and lower bite registration is taken and the bite registration is scanned to obtain the digital record of upper and lower relation. The impression tray system disclosed in U.S. Pat. Nos. 8,277,216; 8,899,983; and 8,998,615 may be used for the bite registration. In another example embodiment, CT scan by having the patient close mouth completely while wearing its existing dentures or other restorations may be taken to directly obtain the digital record.

During step 3, in one example embodiment, by matching each digital record of the upper and lower jaws with the corresponding surface on the digital record of upper and lower jaw relations, the upper and lower jaw records are digitally aligned to simulate the patient's mouth. The scanned impression copings in the digital record of step 1 indicate the implant positions and orientations. According to the simulated patient's mouth, a try-in superstructure is digitally designed by using a plurality of landmarks recorded, and one or more dental bars are digitally recorded by using the recorded implant position and orientation. After digitally designing the dental bars, housing spaces are generated onto a mucosal surface of the try-in superstructure. Each housing space may be shaped to fit with the corresponding dental bar with certain margins. In another example embodiment, the housing space may cover a plurality of dental bars with certain margins.

During step 4, in one example embodiment, the try-in superstructure is produced by a three-dimensional (3D) printer from the digital design of the try-in superstructure produced at step 3. Step 4 further includes fabrication of dental bars. In one example embodiment, the dental bars are produced by milling.

During step 5, in one example embodiment, the dental bars are inserted into the patient's mouth and connected with implants. Step 5 further includes a second impression of the patient's jaw wearing dental bars. An impression material is applied onto mucosal surface of the try-in superstructure, especially around and in housing space, and the try-in superstructure is seated onto dental bars to physically record on the impression of the actual dental bar locations.

During step 6, in one example embodiment, the try-in superstructure with the impression is scanned to obtain the digital record.

During step 7, in one example embodiment, referring to the digital record obtained at step 6, the housing spaces are adjusted and/or generated. Each adjusted housing space is designed to fit with the corresponding dental bar with certain margin. If other adjustments are required, such as midline or occlusal plane, such adjustments are also made to make a digital design of a final superstructure.

During step 8, the final superstructure is fabricated. In one example embodiment, the final superstructure is fabricated by milling from an acrylic block or a ceramic or zirconia block. In another example embodiment, the final superstructure is fabricated by 3D printing.

Although the invention has been described in detail with particular reference to some embodiments, other embodiments can achieve the same or similar results. Upon studying this application, those skilled in the art will realize other equivalent variations and/or modifications that can also be used. It is intended that the claims contained in any patent issued on this application cover all such equivalents. The entire disclosures of all references, applications, patents, and publications cited above are hereby incorporated herein by reference.

What is claimed is:

1. An apparatus for implant-bar-supported restoration, the apparatus comprising a superstructure and a plurality of dental bars,
   wherein at least two of the plurality of dental bars have different shapes and different sizes,
   wherein the plurality of dental bars are positioned on the superstructure to be spaced apart from one another;
   wherein the superstructure is coupled with the plurality of dental bars such that a plurality of gaps are formed between the plurality of dental bars coupled to the superstructure, each gap formed between two different dental bars,
   wherein each of the plurality of dental bars comprises at least one implant interface and a beam structure, and
   wherein the at least one implant interface is protrudingly formed from a bottom surface of the beam structure and shaped and configured to be inserted into a dental implant fixed to a patient's gum.

2. The apparatus of claim 1, wherein
   the dental implant has a receiving portion shaped and configured to receive the at least one implant interface.

3. The apparatus of claim 2, wherein the superstructure comprises at least one housing space shaped and configured to receive the plurality of dental bars such that the plurality of dental bars are directly coupled to the superstructure.

4. The apparatus of claim 3, wherein the superstructure is coupled with at least one of the plurality of dental bars by at least one of:
   at least one screw that passes through a hole formed through the superstructure and a receiving portion formed on the at least one of the plurality of dental bars; or
   a dental material filling a space between the at least one housing space and a corresponding one of the plurality of dental bars.

5. The apparatus of claim 2, wherein a buccal side surface of the beam structure is inclined with respect to a top surface of the dental bar such that buccal side surfaces of all of the beam structures of the plurality of dental bars have a substantially same angulation.

6. The apparatus of claim 5, wherein lingual surfaces of all of the beam structures have a substantially same angulation with respect to top surfaces of the plurality of dental bars.

7. The apparatus of claim 2, wherein at least one of a buccal side surface or a lingual side surface of the beam structure is inclined with respect to a central axis that passes through a corresponding implant interface of the dental bar.

8. The apparatus of claim 2, wherein the dental bar further comprises at least one step structure on a buccal, lingual, mesial or distal side of the dental bar.

9. The apparatus of claim 2, wherein the dental bar further comprises at least one groove or recess formed on at least one side surface.

10. The apparatus of claim 2, wherein the dental bar further comprises at least one through hole formed from a top surface of the beam structure through a bottom surface of the implant interface, wherein the at least one through hole is configured to receive a first screw for coupling the dental bar with the dental implant.

11. The apparatus of claim 10, wherein at least one of the plurality of dental bars further comprises a receiving portion configured to receive a second screw for coupling the dental bar with the superstructure.

12. The apparatus of claim 2, wherein the beam structure comprises a buccal side surface that is formed as a single surface and a lingual surface that is formed to have two surfaces that are angled.

13. The apparatus of claim 2, wherein the each of the plurality of dental bars is securely coupled to the dental implant by a screw that passes through a through hole formed at the beam structure and the implant interface of the dental bar, the screw tightened into the receiving portion of the dental implant.

14. The apparatus of claim 13, wherein a central axis of the implant interface is aligned with a central axis of the dental implant when the implant interface is properly inserted into the receiving portion of the dental implant.

15. The apparatus of claim 1, wherein each of the plurality of dental bars has a different length.

16. The apparatus of claim 15, wherein each of the plurality of dental bars is shaped and configured to be coupled with a corresponding dental implant.

17. The apparatus of claim 16, wherein the plurality of dental bars coupled with respectively corresponding dental implants are arranged such that sizes of gaps between two different dental bars are different.

18. The apparatus of claim 1, wherein a number of the plurality of dental bars is at least three or four.

19. A dental bar comprising a plurality of separate pieces, wherein:
    each of the plurality of pieces is shaped and configured to be coupled with a dental implant fixed to a patient's gum and having a receiving portion shaped and configured to receive a corresponding one of the plurality of pieces;
    each of the plurality of pieces is shaped and configured to be coupled with a superstructure;
    each of the plurality of pieces has a different shape and a different size;
    the plurality of pieces coupled with the superstructure are positioned to be spaced apart from one another;
    a plurality of gaps are formed between the plurality of pieces coupled to the superstructure, each gap formed between two different pieces;
    each of the plurality of pieces comprises an implant interface and a beam structure; and
    the implant interface is protrudingly formed from a bottom surface of the beam structure and shaped and configured to be inserted into the dental implant fixed to the patient's gum.

20. The dental bar of claim 19, wherein:
    the superstructure comprises a denture;
    at least one of the plurality of pieces is curved according to a curved shape of the superstructure;
    the beam structure is shaped to be inserted into a corresponding housing space formed at the superstructure;
    the implant interface is not centrally formed at the bottom surface of the beam structure;
    a through hole is formed at each of the plurality of pieces, the through hole passing through the beam structure and the implant interface such that a first fastening means inserted into the through hole is received at the receiving portion of the dental implant, the first fastening means securing coupling of the plurality of pieces with the dental implant; and
    each of at least two, but not all, of the plurality of pieces further comprise a receiving portion for receiving a second fastening means for securing coupling of the plurality of pieces with the superstructure, the second fastening means passing through a through hole formed at the superstructure.

* * * * *